(12) United States Patent
Asaoka (10) Patent No.: US 9,766,059 B2
(45) Date of Patent: Sep. 19, 2017

(54) CURVE SENSOR (71) Applicant: OLYMPUS CORPORATION, Tokyo (JP)

(72) Inventor: Nobuyoshi Asaoka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 210 days.

(21) Appl. No.: 14/570,176

(22) Filed: Dec. 15, 2014

(65) Prior Publication Data

US 2015/0100000 A1    Apr. 9, 2015

Related U.S. Application Data (63) Continuation of application No. PCT/JP2013/066869, filed on Jun. 19, 2013.

(30) Foreign Application Priority Data

Jun. 20, 2012 (JP) .................. 2012-138925

(51) Int. Cl.
*A61B 1/00* (2006.01)
*G01B 11/24* (2006.01)
(Continued)

(52) U.S. Cl.
CPC .......... *G01B 11/24* (2013.01); *A61B 1/00013* (2013.01); *A61B 1/00135* (2013.01);
(Continued)

(58) Field of Classification Search
CPC .... A61B 1/00135; A61B 5/1076; G01B 11/24
See application file for complete search history.

(56) References Cited

U.S. PATENT DOCUMENTS

2006/0045408 A1* 3/2006 Jones ................. E21B 17/01
385/12
2007/0116415 A1* 5/2007 Kobayashi ............... A61B 5/06
385/116
(Continued)

FOREIGN PATENT DOCUMENTS

CA    WO 9429671 A1 *  12/1994  ............. G01B 11/18
EP    1 635 034 A1    3/2006
(Continued)

OTHER PUBLICATIONS

International Search Report dated Sep. 24, 2013 issued in PCT/JP2013/066869.
(Continued)

*Primary Examiner* — Michael C Stout
*Assistant Examiner* — Nicholas E Kolderman
(74) *Attorney, Agent, or Firm* — Scully, Scott, Murphy & Presser, P.C.

(57) ABSTRACT

A curve sensor universally applicable to even a curving measurement target having a relatively small diameter is provided. A curve sensor to measure the curving of a curving measurement target includes a light supply unit which guides light, a curve measurement unit which includes a curved state detection unit and which measures the curved state of the measurement target by the change in the amount of light output through the curved state detection unit, a light transmission unit which transmits the light from the light supply unit to the curve measurement unit and a holding portion which holds the light supply unit and the curve measurement unit at predetermined positions on the measurement target.

26 Claims, 8 Drawing Sheets (51) Int. Cl.
- A61B 1/018 (2006.01)
- A61B 5/107 (2006.01)
- G02B 23/24 (2006.01)
- G01B 11/16 (2006.01)
- G02B 23/26 (2006.01)

(52) U.S. Cl.
CPC ............ *A61B 1/018* (2013.01); *A61B 5/1076* (2013.01); *G01B 11/18* (2013.01); *G02B 23/2469* (2013.01); *G02B 23/2476* (2013.01); *G02B 23/26* (2013.01); *A61B 1/00165* (2013.01)

(56) References Cited

U.S. PATENT DOCUMENTS

| | | | |
|---|---|---|---|
| 2009/0123111 A1 | 5/2009 | Udd | |
| 2010/0134782 A1* | 6/2010 | Roberts | E21B 17/015 356/32 |
| 2010/0298895 A1* | 11/2010 | Ghaffari | A61B 1/00082 607/3 |
| 2011/0098533 A1* | 4/2011 | Onoda | A61B 1/0051 600/117 |
| 2013/0096572 A1* | 4/2013 | Donhowe | A61B 34/10 606/130 |
| 2013/0201485 A1* | 8/2013 | Rubio-Guivernau | G01B 9/02091 356/479 |

FOREIGN PATENT DOCUMENTS

| | | |
|---|---|---|
| JP | H05-91972 A | 4/1993 |
| JP | 2005-027725 A | 2/2005 |
| JP | 2007-044405 A | 2/2007 |
| JP | 2007-044412 A | 2/2007 |
| JP | 3881525 B2 | 2/2007 |
| JP | 3881526 B2 | 2/2007 |
| JP | 3898910 B2 | 3/2007 |
| JP | 4005318 B2 | 11/2007 |
| WO | 94/29671 A1 | 12/1994 |
| WO | 2004/056017 A1 | 7/2004 |

OTHER PUBLICATIONS

English Abstract of JP 2002-345729, dated Dec. 3, 2002.
English Abstract of JP 2002-345730, dated Dec. 3, 2002.
English Abstract of JP 2002-355215, dated Dec. 10, 2002.
English Abstract of JP 2002-253481, dated Sep. 10, 2002.
English translation of International Preliminary Report on Patentability together with the Written Opinion dated Dec. 31, 2014 received in related International Application No. PCT/JP2013/066869.
Chinese Office Action dated Dec. 24, 2015 from related Chinese Patent Application No. 201380027015.0 , together with an English language translation.
Extended Supplementary European Search Report dated Jan. 28, 2016 from related European Application No. 13 80 7866.2.
Japanese Office Action dated Apr. 12, 2016 in Japanese Patent Application No. 2012-138925.

* cited by examiner

CURVE SENSOR

CROSS-REFERENCE TO RELATED APPLICATIONS

This application is a Continuation Application of PCT Application No. PCT/JP2013/066869, filed Jun. 19, 2013 and based upon and claiming the benefit of priority from Japanese Patent Application No. 2012-138925, filed Jun. 20, 2012, the entire contents of all of which are incorporated herein by references.

BACKGROUND OF THE INVENTION

1. Field of the Invention

The present invention relates to a curve sensor to detect the curved state of a curving measurement target.

Background Art

2. Description of the Related Art

A curve sensor to detect the curved state (curving angle or curving direction) of a curving measurement target is generally known. For example, such a curve sensor guides light having a predetermined optical characteristic emitted from a light source to an optical fiber provided with a curved state detecting unit. At this time, the light amount in the curved state detecting unit changes in accordance with the curving angle and curving direction of the optical fiber. Based on the change in the light amount, the curved state of the optical fiber, thereby the curved state of the curving measurement target is detected.

As an example of such a curve sensor, Jpn. Pat. Appln. KOKAI Publication No. 2007-44412 has disclosed an endoscope insertion shape detection probe to detect the shape of an insertion tube of an endoscope. The probe comprises a probe body, and a module connected to the probe body. The outer diameter of the probe body is formed to be less than the inner diameter of a forceps channel in the endoscope. The probe body comprises a light supply fiber, curvature detection fibers provided with light loss portions, and a mirror disposed at the distal ends of the light supply fiber and the curvature detection fibers.

When the insertion shape of the endoscope is detected, the probe body is first inserted into the forceps channel in the endoscope. Light emitted from a light source is then guided by the light supply fiber and reflected by the mirror at the distal end. The reflected light is then guided by the curvature detection fibers, and received on a module side from the proximal end of the curvature detection fibers. The amount of the light guided by the curvature detection fibers has changed by the leakage of the light in the light loss portions, and the curving angle or curving direction of the curvature detection fibers at the light loss portions is detected on the basis of the amount of the light received on the module side. In this way, the insertion shape of the endoscope in which the probe body is inserted is detected.

BRIEF SUMMARY OF THE INVENTION

According to an embodiment of the present invention, there is provided a curve sensor which measures the curving of a curving measurement target, the curve sensor comprising: a light supply unit which guides light; a curve measurement unit which comprises a curved state detection unit and which measures the curved state of the measurement target by the change in the amount of light output through the curved state detection unit; a light transmission unit which transmits the light from the light supply unit to the curve measurement unit; and a holding portion which holds the light supply unit and the curve measurement unit at predetermined positions on the measurement target.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE PREFERRED EMBODIMENT

Hereinafter, embodiments of the present invention will be described with reference to the drawings.

First Embodiment

Figure 1:
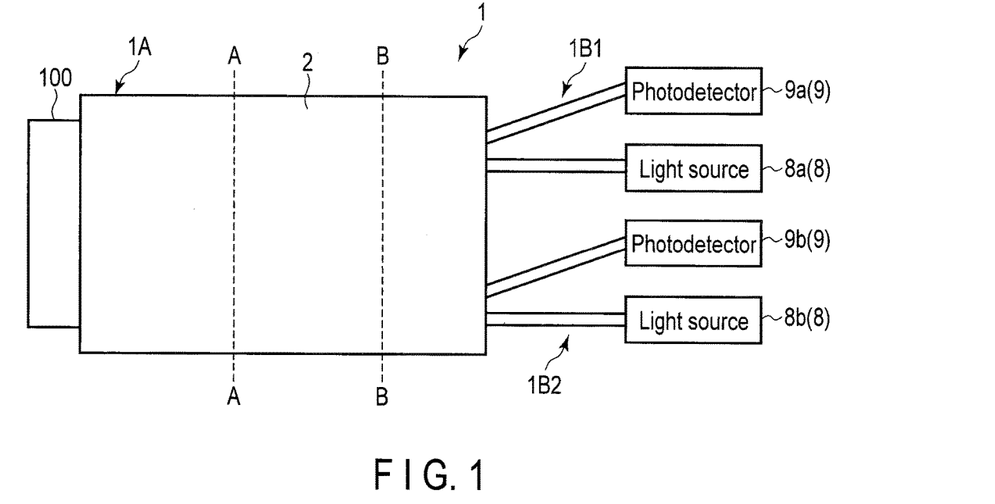
FIG. 1 is a diagram schematically showing a curve sensor according to a first embodiment.

FIG. 1 is a diagram schematically showing a curve sensor 1 according to the first embodiment. The curve sensor 1 comprises a cylindrical body 1A and two sensor units 1B1 and 1B2. The cylindrical body 1A comprises a cylindrical first elastic member 2 and a cylindrical second elastic member 3. The inner diameter of the first elastic member 2 is set to be substantially equal to the outer diameter of the second elastic member 3. The first elastic member 2 is engaged with the outer side of the second elastic member 3 in an externally fit state, and the outer circumferential surface of the second elastic member 3 is joined to the inner circumferential surface of the first elastic member 2. A curving measurement target 100 such as a flexible endoscope having a flexible curving portion, a forceps, or a catheter is inserted into the inside of the second elastic member 3. The inner diameter of the second elastic member 3 is set to be substantially adaptive to the outer diameter of the measurement target 100 to be inserted.

When the curve sensor 1 is attached to the curving measurement target 100, the inner circumferential surface of the second elastic member 3 is joined to the outer circumferential surface of the curving measurement target 100. At this time, the curve sensor 1 is held and fixed to the outer circumferential surface of the curving measurement target 100 by the elastic force of the first and second elastic members 2 and 3.

Figure 2:
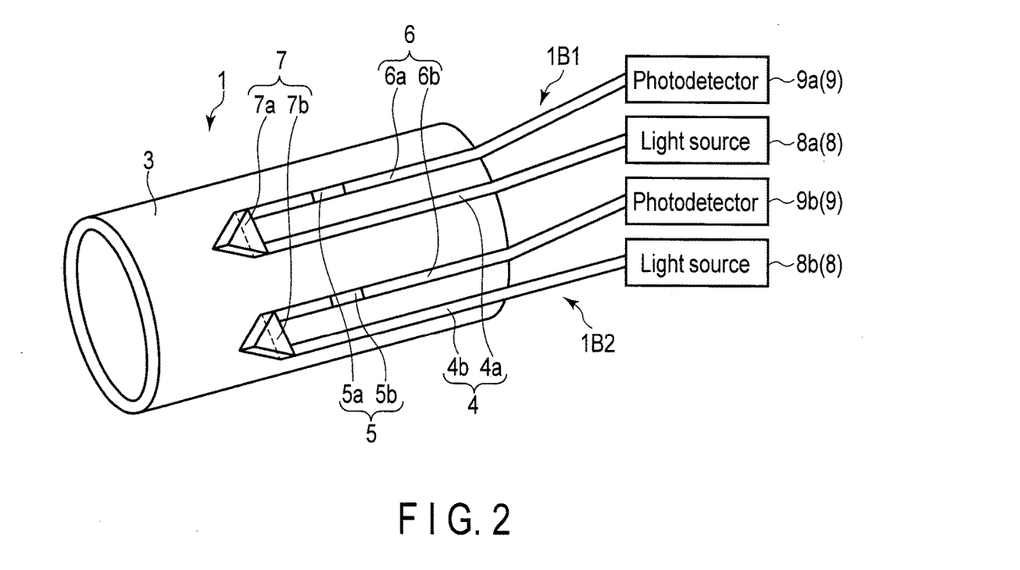
FIG. 2 is a perspective view schematically showing the curve sensor where a first elastic member is removed.
Figure 3:
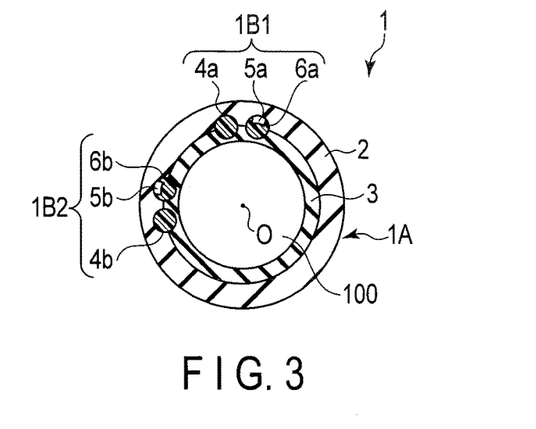
FIG. 3 is a cross sectional view showing the curve sensor according to the first embodiment taken along the line A-A in FIG. 1.

FIG. 2 is a perspective view schematically showing the curve sensor 1 where the first elastic member 2 is removed. FIG. 3 is a cross sectional view showing the curve sensor 1 taken along the line A-A in FIG. 1. The curve sensor 1 comprises a light supply fiber 4 as a light supply unit, a sensor fiber 6 as a curve measurement unit provided with a curved state detection unit 5, and a reflecting member 7 as a light transmission unit. The light supply fiber 4, the sensor fiber 6, and the reflecting member 7 are inserted between the first elastic member 2 and the second elastic member 3, and in this state, held and fixed by the elastic force of the first and second elastic members 2 and 3. The light supply fiber 4, the sensor fiber 6, and the reflecting member 7 may be further fixed by an adhesive agent not shown.

The light supply fiber 4 and the sensor fiber 6 are, for example, optical fibers each including, for example, a glass core and a resin cladding. The curved state detection unit 5 is formed by, for example, providing a cutout in the cladding at a predetermined position of the sensor fiber 6 and filling the cutout with a resin having a predetermined optical characteristic (e.g. an absorber or fluorescent material which absorbs light of a predetermined wavelength).

The reflecting member 7 is disposed on the longitudinally distal side of the light supply fiber 4 and the sensor fiber 6, and reflects the light guided from the light supply fiber 4 to the sensor fiber 6. That is, the light supply fiber 4 and the sensor fiber 6 are optically connected to each other via the reflecting member 7. The reflecting member 7 is, for example, a prism, and is a member which includes two mirrors that intersect at right angles with each other and which reverses the direction of light 180 degrees.

A light source 8 is connected to the longitudinally proximal side of the light supply fiber 4. The light source 8 is, for example, a laser light source, and emits laser light having a predetermined wavelength to the light supply fiber 4. A photodetector 9 is connected to the longitudinally proximal side of the sensor fiber 6. The photodetector 9 receives the light guided by the light supply fiber 4, reflected by the reflecting member 7, and guided by the sensor fiber 6. That is, the photodetector 9 is a light receiving unit which receives a light signal (curve signal) regarding the curved state from the sensor fiber 6.

In FIG. 1 to FIG. 3, two light supply fibers 4a and 4b, two sensor fibers 6a and 6b respectively provided with curved state detection units 5a and 5b, and two reflecting members 7a and 7b are shown. Light sources 8a and 8b are respectively connected to the proximal sides of the light supply fibers 4a and 4b. Photodetectors 9a and 9b are respectively connected to the proximal sides of the sensor fibers 6a and 6b.

As shown in FIG. 3, the curved state detection unit 5a and the curved state detection unit 5b are disposed at positions that intersect at right angles with each other in the radial direction of the curve sensor 1, that is, in the X-axis direction and the Y-axis direction that intersect at right angles with each other with respect to a central line O of the cylindrical body 1A of the curve sensor 1 in a plane that intersects at right angles with the direction of the central line O, and respectively detect a curve in the up and down direction and a curve in the right and left direction. That is, the curve sensor 1 is capable of measuring curves in two axial directions that intersect at right angles with each other by the curved state detection units 5a and 5b.

However, the positional relation between the curved state detection unit 5a and the curved state detection unit 5b is not limited to 90 degrees in the present embodiment, and the curved state detection units 5a and 5b may be arranged by a positional relation other than 90 degrees. For example, a configuration having the curved state detection unit 5a alone to measure a curve in one axial direction is also possible.

When the curved state of the curving measurement target 100 is detected, the curving measurement target 100 is first inserted into the second elastic member 3 of the curve sensor 1, and the curve sensor 1 is attached to the outer circumferential surface of the curving measurement target 100 by the elastic force of the first and second elastic members 2 and 3. That is, the first and second elastic members 2 and 3 function as holding portions (holding members) which hold a curve detection mechanism including the light supply fiber 4, the sensor fiber 6, and the reflecting member 7 to predetermined positions on the curving measurement target 100.

The light emitted from the light source 8 is then guided by the light supply fiber 4, reflected by the reflecting member 7 disposed on the distal side of the light supply fiber 4, and the reflected light is guided by the sensor fiber 6. Further, when the reflected light has passed through the curved state detection unit 5 of the sensor fiber 6, the amount of light leaking out from the curved state detection unit 5 changes in accordance with the curving angle or the curving direction. The changed amount of light is received by the photodetector 9 on the proximal side of the sensor fiber 6. In this way, the curved state of the curving measurement target 100 in the vicinity of the curved state detection unit 5 is detected. That is, the curved state of the curving measurement target 100 can be measured by the change in the amount of the light which is output through the curved state detection unit 5.

According to the present embodiment, the light supply fiber 4 and the sensor fiber 6 provided with the curved state detection unit 5 are held to the predetermined positions on the curving measurement target 100 by the elastic force of the first elastic member 2 and the second elastic member 3. Consequently, the curve detection mechanism including the curved state detection unit can be easily fixed to the curving measurement target, and a curve sensor universally attachable to even a measurement target having a relatively small diameter can be provided.

The curve sensor according to the present embodiment can be attached not to the inside of the endoscope, for example, to a forceps channel of the endoscope but to the outer circumferential surface of the endoscope. Therefore, even if the curving measurement target does not have a longitudinally extending through-hole such as the forceps channel, the curve sensor can be easily incorporated into the curving measurement target.

For example, in an endoscope having a forceps channel, it may be necessary to monitor the curved state of the endoscope while working by using the forceps channel. This work may be, for example, in a bladder endoscope, to monitor the curved state of the endoscope to know which part of a bladder the endoscope is facing while supplying water to or discharging water from the bladder through the forceps channel. In this case as well, it is possible to attach the curve sensor to the curving measurement target to detect the curved state of the curving measurement target regardless of the forceps channel. That is, it is possible to easily detect the curved state of the curving measurement target while working by using the forceps channel.

In the present embodiment, it is assumed that a user can freely attach or detach the curve sensor to or from the existing curving measurement target. The advantage in this case is that the user can attach the curve sensor after having purchased the curving measurement target without repurchasing another curving measurement target. Moreover, the user can detach the curve sensor from the curving measurement target, that is, the holding portions are attachable to and detachable from the curving measurement target. The advantage is therefore that the curve sensor can be restored to the state of having no curving measurement target, that is, the user has more options. The light supply unit and the curve measurement unit are held at the predetermined positions of the holding portion whether the holding portion is attached to or detached from the curving measurement target.

When the curve sensor is attached to a curving measurement target having a relatively small diameter, the mechanical or optical adverse effects of, for example, the rigidity of the components of the attached curve sensor on curving become less negligible if the curving measurement target is thinner. According to the present embodiment, it is possible to provide a curve sensor which is attachable to even a curving measurement target having a relatively small diameter without inhibiting its curving performance. Moreover, the curved state detection unit can be properly protected by the first and second elastic members as the holding portions.

The present embodiment is not limited to the above description, and a manufacturer may previously attach the curve sensor to the existing curving measurement target without leaving to the user. In this case, the curve sensor may be fixed to the curving measurement target by, for example, an adhesive agent or solder so that the curve sensor cannot be detached from the curving measurement target. This configuration is preferred when user convenience is taken into account for, for example, a disposable curving measurement target or a micro curving measurement target.

The cores of the light supply fiber 4 and the sensor fiber 6 are not exclusively made of glass and may be made of a resin. If these fibers are made of a resin, the elasticity of the fibers increases, so that the fibers can more easily curve in accordance with the curving of the first elastic member 2 and the second elastic member 3. Therefore, when the curve sensor 1 has curved, the light supply fiber 4 and the sensor fiber 6 do not easily inhibit the curving between the first elastic member 2 and the second elastic member 3. Thus, the curve sensor 1 can easily adapt to a larger curving angle.

(First Modification of First Embodiment)

Figure 4:
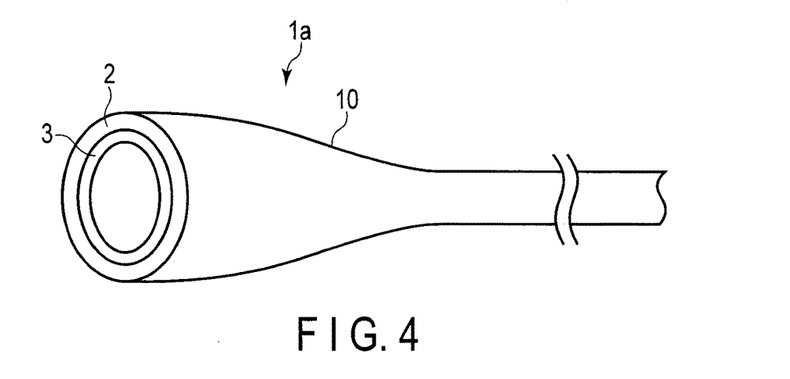
FIG. 4 is a diagram schematically showing a curve sensor according to a first modification of the first embodiment.

FIG. 4 is a diagram schematically showing a curve sensor 1*a* according to a first modification of the first embodiment. In the present modification, the curve sensor 1*a* has a tapered portion 10 on one end side. The tapered portion 10 gradually expands so that each of the inner diameters of the first elastic member 2 and the second elastic member 3 increases toward the terminal portion on one end side.

In the present modification, when the curving measurement target 100 is inserted into the inside of the second elastic member 3, the curving measurement target 100 is guided to the expanded part of the tapered portion 10. As a result, the operation of inserting the curving measurement target 100 into the inside of the second elastic member 3 is easier.

The tapered portion 10 is not exclusively provided on one end side of the curve sensor 1*a*, and may be provided on both sides. The tapered portion 10 may be cut out on one end side of the first and second elastic members 2 and 3 so that the outer diameter of the tapered portion 10 is not excessively large.

The tapered portion 10 is not exclusively cut out. For example, one end of each of the first and second elastic members 2 and 3 may be cut out so that this end is easily elastically deformed to a great degree. In this case as well, the operation of inserting the curving measurement target 100 into the inside of the second elastic member 3 is easier.

(Second Modification of First Embodiment)

Figure 5A:
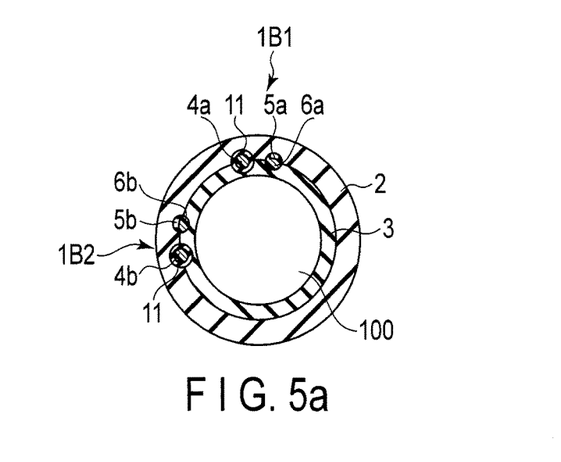
FIG. 5a is a cross sectional view showing a curve sensor according to a second modification of the first embodiment taken along the line A-A in FIG. 1.
Figures 5B, 6:
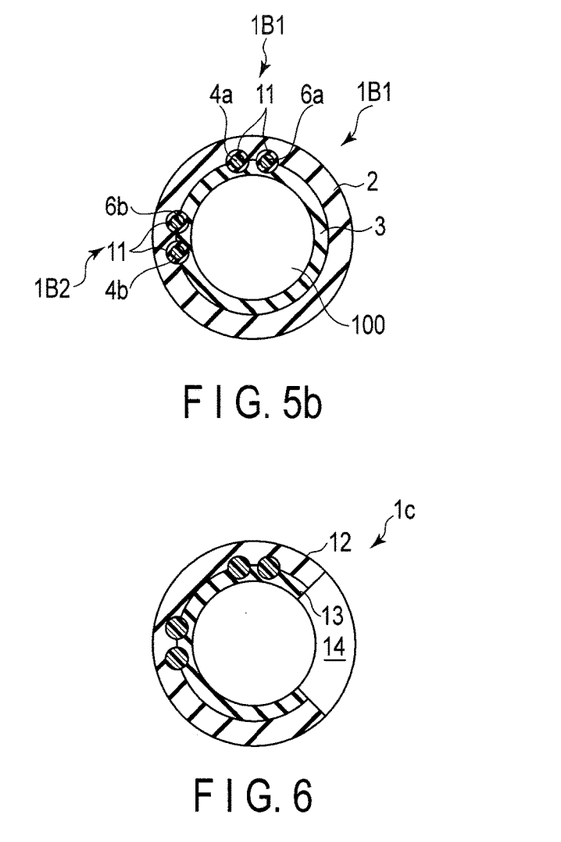
FIG. 5b is a cross sectional view showing the curve sensor according to the second modification of the first embodiment taken along the line B-B in FIG. 1.
FIG. 6 is a cross sectional view showing a curve sensor according to a third modification of the first embodiment.

FIG. 5*a* and FIG. 5*b* are cross sectional views showing a curve sensor 1*b* according to a second modification of the first embodiment. In the present modification, thin circular-tube-shaped elastic tubes 11 are fixed between the first elastic member 2 and the second elastic member 3 by an adhesive agent not shown. The light supply fibers 4*a* and 4*b* and the sensor fibers 6*a* and 6*b* are inserted through the elastic tubes 11. As shown in FIG. 5*a*, the parts of the sensor fibers 6*a* and 6*b* where the curved state detection unit 5 is provided are not covered with the elastic tubes 11. The inner diameter of the elastic tubes 11 is larger than the outer diameters of the light supply fibers 4*a* and 4*b* and the sensor fibers 6*a* and 6*b*. Therefore, the light supply fibers 4*a* and 4*b* and the sensor fibers 6*a* and 6*b* are slidable through the elastic tubes 11 in the optical axis direction (longitudinal direction) of the fibers.

The elastic tubes 11 do not extend to both ends of the first elastic member 2. Therefore, the light supply fibers 4*a* and 4*b* and the sensor fibers 6*a* and 6*b* are fixed to the first and second elastic members 2 and 3 by, for example, an adhesive agent at both ends.

According to the present modification, the light supply fiber 4 and the sensor fiber 6 slide through the elastic tube 11 in the optical axis direction, the light supply fiber 4 and the sensor fiber 6 easily curve in accordance with the curving of the first and second elastic members 2 and 3. Therefore, the light supply fiber 4 and the sensor fiber 6 do not easily inhibit the curving of the whole curve sensor 1b. Thus, the curve sensor 1b can easily adapt to a larger curving angle.

(Third Modification of First Embodiment)

FIG. 6 is a cross sectional view showing a curve sensor 1c according to a third modification of the first embodiment. In the present modification, the cross sections of first and second elastic members 12 and 13 are not circular but are C-shaped. That is, a cutout 14 is formed in the circumferential walls of the first and second elastic members 12 and 13.

According to the present modification, the cutout 14 is formed in the first and second elastic members 12 and 13, so that the curve sensor 1c can be attached to a curving measurement target from the side. Thus, the curve sensor 1c is easily attached to the curving measurement target. The present modification is particularly suited to the case where the elastic members are metal spring members.

In the present modification as well, the curved state detection unit 5 is disposed where the cutout 14 is not present, so that the curved state detection unit 5 is protected by the first and second elastic members 12 and 13 as the holding portions. Since the cutout 14 is formed, the rigidity of the first and second elastic members 12 and 13 is lower, and the curving is easier.

Figure 7:
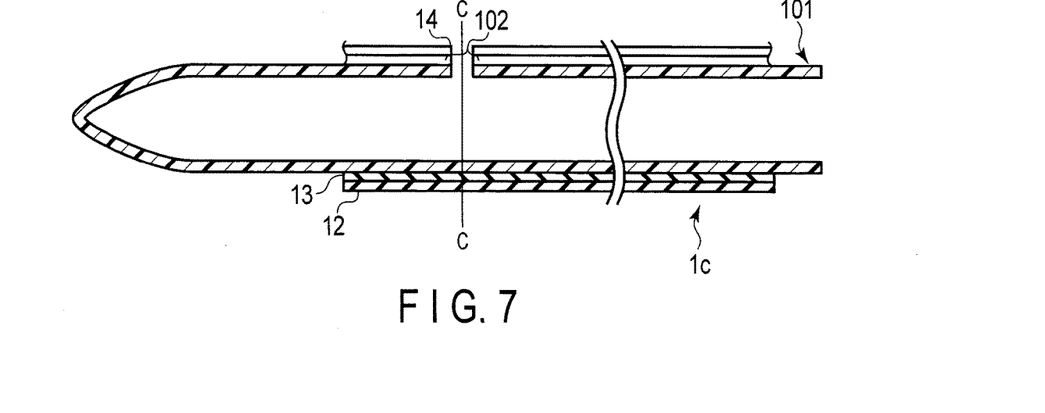
FIG. 7 is a longitudinal sectional view schematically showing a catheter to which the curve sensor according to the third modification of the first embodiment is attached.
Figure 8:
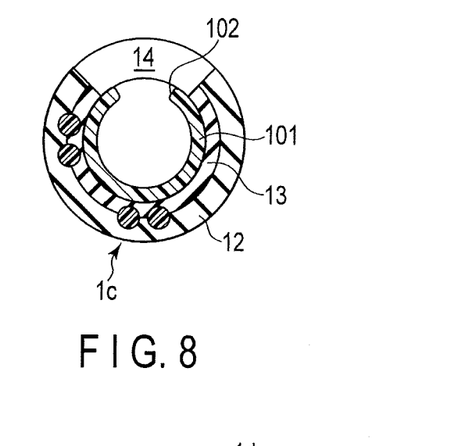
FIG. 8 is a cross sectional view taken along the line C-C in FIG. 7.

The curve sensor 1c according to the present modification is suitably attached to a curving measurement target smaller in diameter than the endoscope, for example, a catheter which is inserted into a living tissue. FIG. 7 is a longitudinal sectional view schematically showing a catheter 101 to which the curve sensor 1c is attached. FIG. 8 is a cross sectional view taken along the line C-C in FIG. 7. On the circumferential surface of the catheter 101, a through-hole 102 which radially pierces the outer circumferential surface is formed. The through-hole 102 is, for example, a discharge hole for a drug to administer the drug to the living tissue by using the catheter 101, or a suction hole to suck a body fluid or the like from the living tissue.

At the time of attachment, the cutout 14 in the first and second elastic members 12 and 13 of the curve sensor 1c is aligned with the through-hole 102 of the catheter 101 so that the curve sensor 1c does not cover the through-hole 102 of the catheter 101, and the curve sensor 1c is then attached to the catheter 101.

The curve sensor 1c is thus attached after the through-hole 102 of the catheter 101 is aligned with the cutout 14 of the curve sensor 1c. Consequently, the curve sensor 1c according to the present modification can be applied to the catheter 101 without inhibiting the function of the catheter 101.

(Fourth Modification of First Embodiment)

Figure 9:
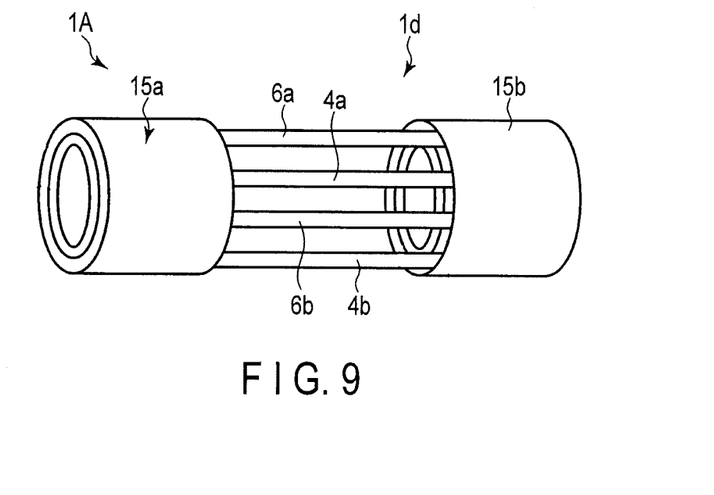
FIG. 9 is a perspective view schematically showing a curve sensor according to a fourth modification of the first embodiment.

FIG. 9 is a diagram schematically showing a curve sensor 1d according to a fourth modification of the first embodiment. In the present modification, the cylindrical body 1A is separated into a distal side cylindrical body 15a and a proximal side cylindrical body 15b. That is, the cylindrical bodies as the holding members comprising elastic members are located apart from each other. The curved state detection unit 5 of the sensor fiber 6 is located in at least one of the distal side cylindrical body 15a and the proximal side cylindrical body 15b. The distal side cylindrical body 15a and the proximal side cylindrical body 15b are coupled to each other by the light supply fiber 4 and the sensor fiber 6 which are held and fixed by these cylindrical bodies.

According to the present modification, the elastic members as the holding portions are not provided in parts of the light supply fiber 4 and the sensor fiber 6, for example, in the part of the sensor fiber 6 where the curved state detection unit 5 is not provided, so that the rigidity of the part is lower.

Therefore, the curving performance of the curve sensor can be improved by the reduced rigidity. In the present modification as well, the curved state detection unit is protected by the first and second elastic members as the holding portions.

Second to seventh embodiments of the present invention are described below. In the following explanation, components similar to those according to the first embodiment are denoted by the same reference signs and are not described.

Second Embodiment

Figure 10:
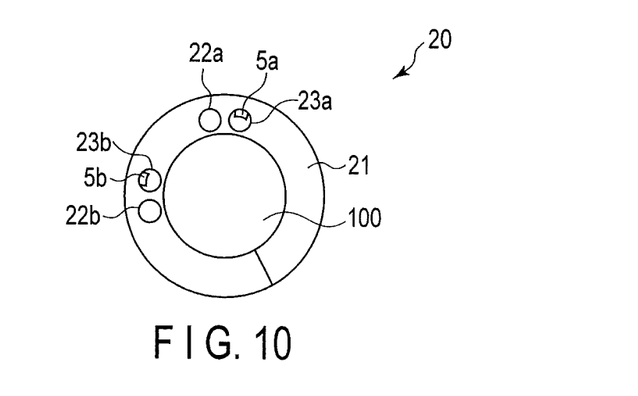
FIG. 10 is a cross sectional view of a curve sensor according to a second embodiment.
Figure 11:
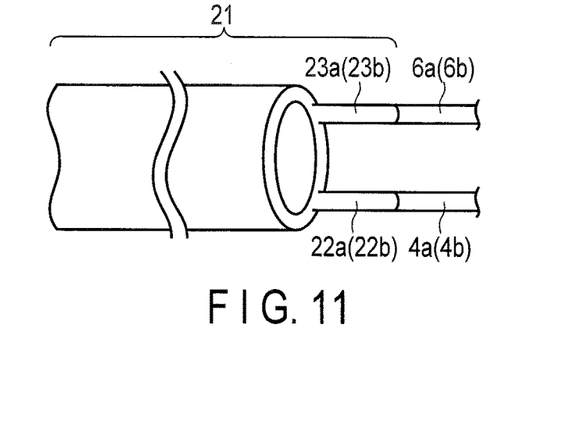
FIG. 11 is a perspective view schematically showing the proximal side of the curve sensor according to the second embodiment.

FIG. 10 and FIG. 11 are diagrams showing a curve sensor 20 according to the second embodiment. In the present embodiment, parts of the light supply fibers 4a and 4b according to the first embodiment are replaced with light supply paths 22a and 22b each including a core and a cladding provided on a flexible optical circuit board 21. At least parts of the sensor fibers 6a and 6b including the curved state detection units 5a and 5b according to the first embodiment are replaced with sensor paths 23a and 23b each including a core and a cladding provided on the flexible optical circuit board 21. The light supply paths 22a and 22b and the light supply fibers 4a and 4b, and the sensor paths 23a and 23b and the sensor fibers 6a and 6b are optically coupled to each other by, for example, fusion bonding.

In the second embodiment, the first and second elastic members 2 and 3 according to the first embodiment are unnecessary. When the curve sensor 20 is attached to the curving measurement target 100, the flexible optical circuit board 21 functions as a holding portion which holds the curve detection mechanism including the curved state detection unit 5 at a predetermined position on the curving measurement target 100.

It is generally difficult for the reasons of costs to produce the flexible optical circuit board 21 that is long enough (e.g. about 1 m long) to be adaptable to the endoscope in the longitudinal direction (optical axis direction) of the curve sensor 20. Thus, as shown in FIG. 11, the sensor is manufactured by adding the light supply fibers 4a and 4b and the sensor fibers 6a and 6b as extension optical fibers to the flexible optical circuit board 21. As a result, even when the length of the flexible optical circuit board 21 is shorter than necessary length, the length of the curve sensor 20 can be extended to necessary length, which provides a configuration advantageous in respect of costs.

According to the present embodiment, the positional relation between the two curved state detection units 5a and 5b is determined by the accuracy of the space between the two sensor paths 23a and 23b of the flexible optical circuit board 21, so that it is not necessary to align the two sensor paths 23a and 23b during assembly. It is also unnecessary to adjust the positional relation between the two curved state detection units 5a and 5b in the circumferential direction of the curve sensor 20. Therefore, the assembly process of the curve sensor 20 can be simpler.

In the present embodiment as well, the curved state detection unit is protected by the flexible optical circuit board. The flexible optical circuit board has the function to bundle the light supply paths and the sensor paths and the function to hold the light supply paths and the sensor paths to the flexible optical circuit board. Since the flexible optical circuit board has these two functions in one member, it is not necessary to increase the components of the curve sensor. Therefore, the rigidity of the curve sensor can be reduced, and the curve sensor easily curves.

If the core and the cladding are made of a resin, a curve sensor having higher curving performance is more easily provided.

(Modification of Second Embodiment)

Figure 12:
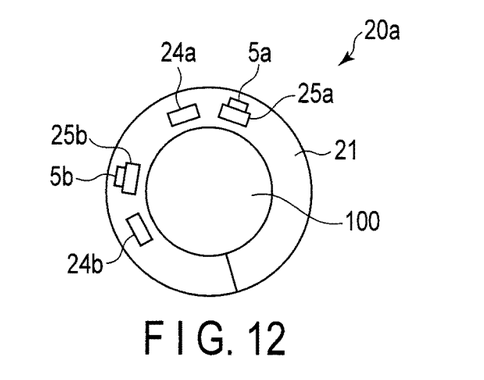
FIG. 12 is a cross sectional view of a curve sensor according to a modification of the second embodiment.

FIG. 12 is a cross sectional view of a curve sensor 20a according to a modification of the second embodiment. In the present modification, the flexible optical circuit board 21 is not limited to the type that uses the light supply paths and the sensor paths of the optical fiber including the core and the cladding. The flexible optical circuit board 21 is, for example, a flexible optical circuit board that uses light supply paths 24a and 24b comprising optical waveguide paths, and the sensor paths 25a and 25b comprising optical waveguide paths. The curved state detection units 5a and 5b are provided in the sensor paths 25a and 25b, which are respectively manufactured in advance in parts of the sensor paths 25a and 25b by, for example, printing during manufacture.

In the present modification as well, the curve sensor having higher curving performance can be provided. The curved state detection unit is protected by the flexible optical circuit board.

Third Embodiment

Figure 13:
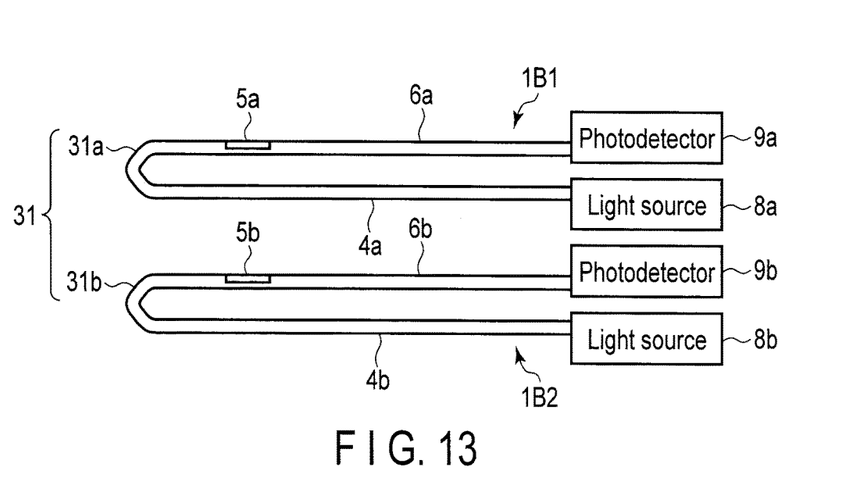
FIG. 13 is a diagram schematically showing a curve sensor according to a third embodiment.

FIG. 13 is a diagram schematically showing a curve sensor 30 according to the third embodiment. In the present embodiment, the light supply fiber 4 and the sensor fiber 6 are formed by one optical fiber. Therefore, the curve sensor 30 does not have the reflecting member 7 according to the first embodiment, and a turnover 31 (31a and 31b) produced by folding one optical fiber along the way is formed. That is, the turnover 31 optically connects the light supply fiber 4 and the sensor fiber 6 without the reflecting member 7 in between.

The curve sensor is not limited to the above, and may be configured by a flexible optical circuit board in which the turnover 31 is formed in advance.

According to the present embodiment, since the reflecting member is not provided, there is no reflection loss of the light guided by the optical fiber, and the curve sensor which is thus high in sensitivity can be provided. Since the configuration of the curve sensor can be simpler, the curve sensor is easily reduced in size and cost.

Fourth Embodiment

Figure 14:
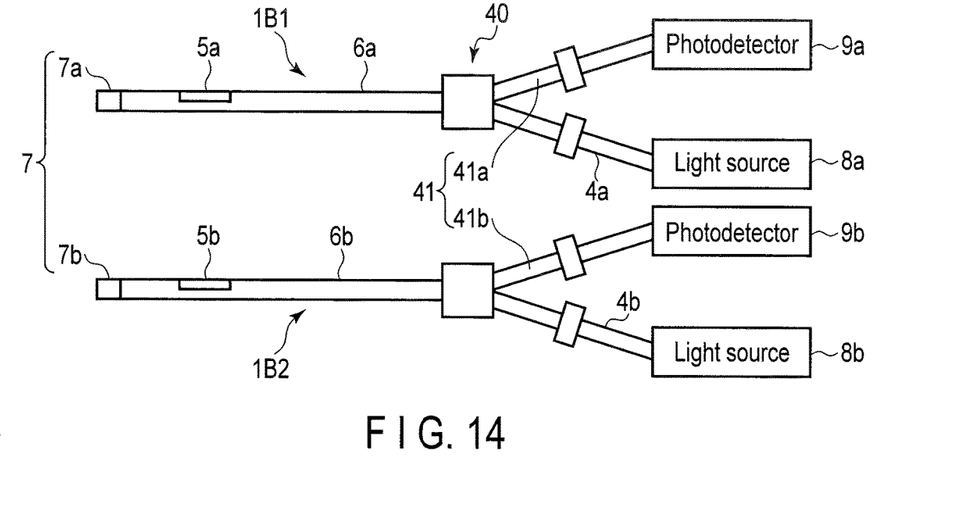
FIG. 14 is a diagram schematically showing a curve sensor according to a fourth embodiment.
Figure 15:
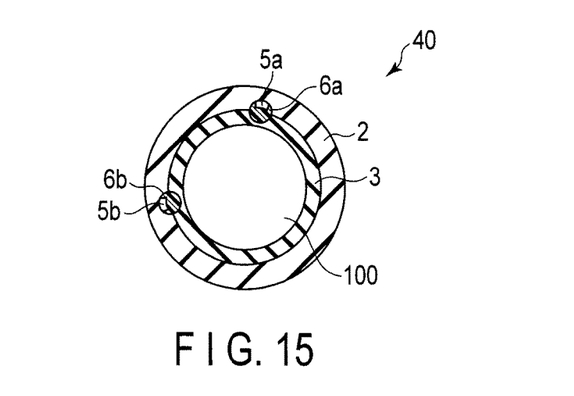
FIG. 15 is a cross sectional view of the curve sensor according to the fourth embodiment.

FIG. 14 and FIG. 15 are diagrams showing a curve sensor 40 according to the fourth embodiment. In the present embodiment, the light supply fiber 4 and the sensor fiber 6 are connected to each other by an optical coupler 41 (41a and 41b), and the light supply fiber 4 and the sensor fiber 6 are combined into one optical fiber. The reflecting member 7 (7a and 7b) is disposed on the distal side of one sensor fiber 6 (6a and 6b).

In the present embodiment, the light guided by the light supply fiber 4 is then guided by the sensor fiber 6 through the optical coupler 41, and the light reflected by the reflecting member 7 is further guided by the sensor fiber 6 and received by the photodetector 9 through the optical coupler 41. The photodetector 9 measures the light amount that is affected by the amount of the light which changes in the curved state detection unit 5 in accordance with the curving state of the sensor fiber 6.

According to the present embodiment, the light supply fiber and the sensor fiber are combined along the way, and at least part of the sensor fiber also serves as the light supply fiber, so that the number of fibers is reduced. Thus, the curve sensor is easily reduced in size. Since the number of fibers used is small, the curve sensor can be manufactured at low cost. Moreover, the curved state detection unit is protected by the first and second elastic members as the holding portions.

Since the light supply fiber does not contact the curving measurement target, the rigidity of the light supply fiber does not easily prevent the curving of the curving measurement target. Moreover, the curve sensor adapted to a large curving angle is easily provided.

Fifth Embodiment

Figure 16:
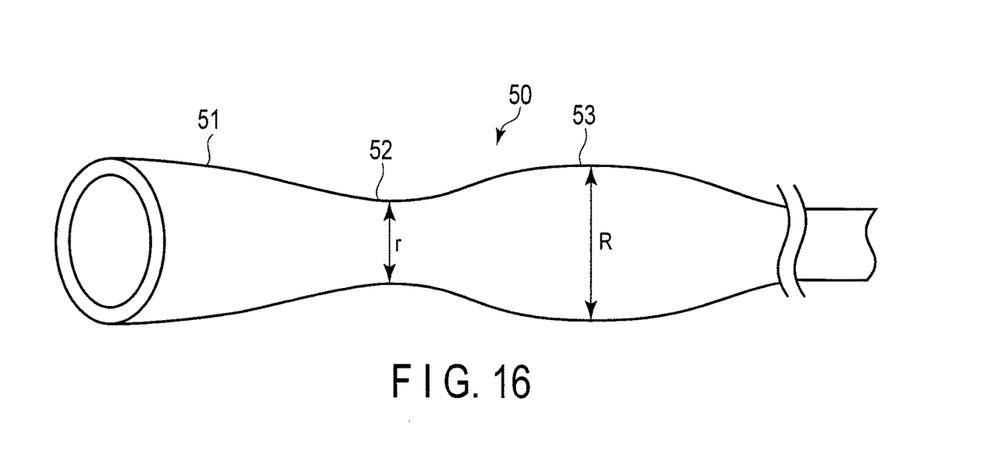
FIG. 16 is a diagram schematically showing a second elastic member of a curve sensor according to a fifth embodiment.

FIG. 16 is a diagram schematically showing a second elastic member 51 of a curve sensor 50 according to the fifth embodiment. In the present embodiment, the second elastic member 51 of the curve sensor 50 has a first region 52 and a second region 53 that have different diameters. The first region 52 is formed by a small diameter portion having a small first diameter r. The second region 53 is formed by a large diameter portion having a second diameter R (r<R) larger than the first diameter r.

The first region 52 is a region where the curved state detection unit 5 of the sensor fiber 6 is disposed. The second region 53 is a region where the curved state detection unit 5 is not disposed, that is, a region different from the region where the curved state detection unit 5 is disposed. The curving measurement target to be inserted into the second elastic member 51 is held by stronger elastic force in the first region 52 than in the second region 53. In the second region 53, the curving measurement target is held by weaker elastic force.

Although not shown, the inner circumferential surface of the first elastic member which is engaged with the outer circumferential surface of the second elastic member 51 substantially adapts to the shape of a second outer circumferential surface, and is configured to hold and fix the curve detection mechanism including the light supply fiber, the sensor fiber, and others between the first and second elastic members.

According to the present embodiment, the region where the curved state detection unit is fixed to the curving measurement target by stronger elastic force is provided. Thus, a correct curving state can be measured, and at the same time, it is possible to easily adapt to a large curving angle.

The optical fiber is held by weaker elastic force in the region where the curved state detection unit is not provided, so that the optical fiber is slidable in this region. Thus, curving is easy.

Sixth Embodiment

Figure 17:
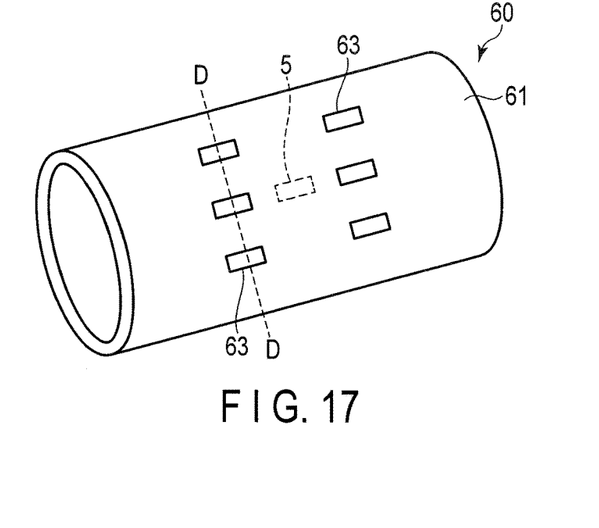
FIG. 17 is a diagram schematically showing a first elastic member of a curve sensor according to a sixth embodiment.
Figure 18:
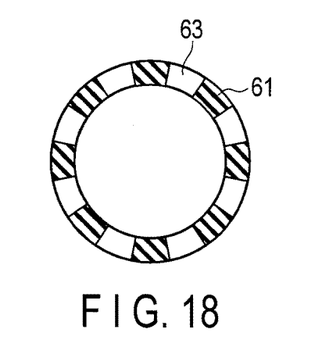
FIG. 18 is a cross sectional view taken along the line D-D in FIG. 17.

FIG. 17 and FIG. 18 are diagrams showing a first elastic member 61 of a curve sensor 60 according to the sixth embodiment. In the present embodiment, at least one slit 63 is formed in the first elastic member 61 and the second elastic member to radially pierce the circumferential walls of these elastic members. For example, the slits 63 are arranged at predetermined intervals in the circumferential direction of the first elastic member 61 and the second elastic member. The shape of the slit 63 is rectangular in FIG. 17, but may be circular or elliptic.

Although the first elastic member 61 alone is shown in FIG. 17 and FIG. 18, the second elastic member also has a similar configuration. The slits 63 are formed at positions different from the position of the curved state detection unit 5 in the longitudinal direction of the first elastic member 61 and the second elastic member. The slits 63 may be only provided in one of the first elastic member 61 and the second elastic member.

According to the present embodiment, the slits are formed at positions (positions where the curved state detection unit is not provided) different from the positions of the first and second elastic members where the curved state detection unit is located, so that the elastic members is reduced in rigidity, and the curving is easier. The curved state detection unit can be properly protected by the first and second elastic members.

Seventh Embodiment

Figure 19:
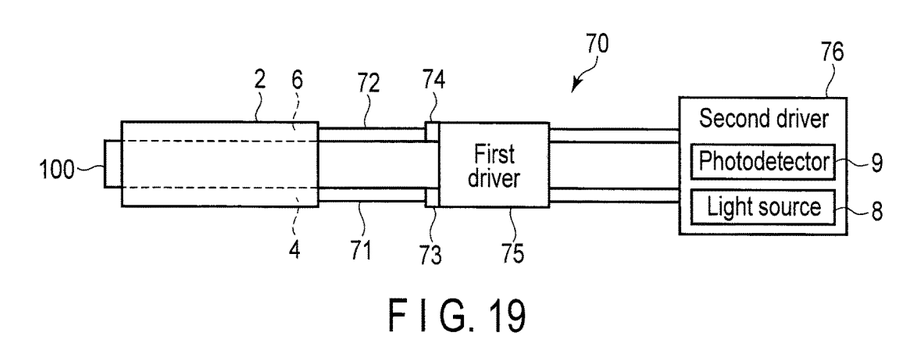
FIG. 19 is a diagram schematically showing one aspect of a curve sensor according to a seventh embodiment.

FIG. 19 is a diagram schematically showing one aspect of a curve sensor 70 according to the seventh embodiment. In the present embodiment, the curve sensor 70 includes an optical fiber 71 which connects the light supply fiber 4 and the light source 8, and an optical fiber 72 which connects the sensor fiber 6 and the photodetector 9. The optical fibers 71 and 72 are connected to a first driver 75 by optical connectors 73 and 74, respectively. The first driver 75 is further connected to a second driver 76 including the light source 8 and the photodetector 9.

According to the present embodiment, the curve sensor can be easily mounted on the curving measurement target. Since the curve sensor is attachable to and detachable from the curving measurement target by the connectors, the curved state detection unit can be easily cleaned.

Figure 20:
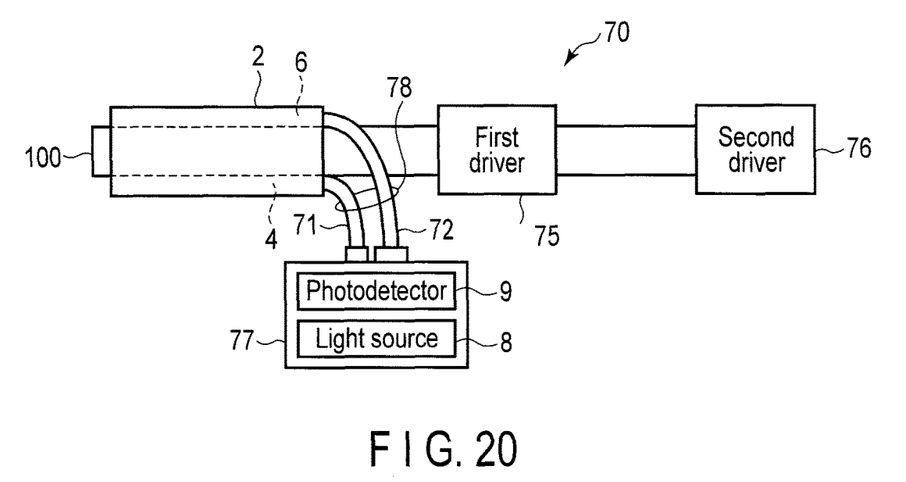
FIG. 20 is a diagram schematically showing another aspect of the curve sensor according to the seventh embodiment.

FIG. 20 is a diagram schematically showing another aspect of the curve sensor 70 according to the seventh embodiment. In the present aspect, the optical fiber 71 and the optical fiber 72 may be bundled by a binder 78 on the middle point of the fibers. The light source 8 and the photodetector 9 may be housed in a separate case 77.

If bundled, the optical fibers are easily handled by an operator. In the present embodiment, the light source and the photodetector do not need to be previously incorporated in the curving measurement target, and the curve sensor higher in versatility can be provided.

While the embodiments and the modifications of the present invention have been described above, the present invention is not limited thereto, and various improvements and changes can be made without departing from the spirit of the invention.

REFERENCE SIGNS LIST

1: curve sensor, 2: first elastic member, 3: second elastic member, 4: light supply fiber, 5: curved state detection unit, 6: sensor fiber, 7: reflecting member, 8: light source, 9: photodetector, 10: tapered portion, 11: elastic tube, 12: first elastic member, 13: second elastic member, 14: cutout, 15*a*: distal side cylindrical body, 15*b*: proximal side cylindrical body, 20: curve sensor, 21: flexible optical circuit board, 22: light supply path, 23: sensor path, 24: light supply path, 25: sensor path, 30: curve sensor, 31: turnover, 40: curve sensor, 41: optical coupler; 50: curve sensor, 51: second elastic member, 52: first region, 53: second region, 60: curve sensor, 61: first elastic member, 62: second elastic member, 63: slit, 70: curve sensor, 71, 72: optical fiber, 73, 74: optical connector, 75: first driver, 76: second driver, 77: case.

What is claimed is:

1. A curve sensor which measures curving of a curving measurement target, the curve sensor comprising:
a light supply unit which guides light;
a curve measurement unit which comprises a curved state detection unit and which measures a curved state of the measurement target by a change in an amount of light output through the curved state detection unit;
a light transmission unit which transmits the light from the light supply unit to the curve measurement unit; and
a holding portion which holds the light supply unit and the curve measurement unit at a predetermined position on the measurement target,
wherein the holding portion is a circular cylindrical body, and the measurement target is inserted into an inside of the cylindrical body, the holding portion comprising:
a cylindrical first holding member, and
a cylindrical second holding member, an outer circumferential surface of the second holding member being engaged with an inner circumferential surface of the first holding member, the measurement target being inserted into the inside of the second holding member,
wherein the holding portion is configured so that at least one of the light supply unit and the curve measurement unit is held between the inner circumferential surface of the first holding member and the outer circumferential surface of the second holding member.

2. The curve sensor according to claim 1, wherein the holding portion comprises a first region and a second region that are different in diameter,
the curved state detection unit of the curve measurement unit is provided in the first region formed by a small diameter portion, and
at least part of the curve measurement unit different from the curved state detection unit is slidably inserted through the second region formed by a large diameter portion.

3. The curve sensor according to claim 1, wherein the holding portion fixes and holds, to the measurement target, the part of the curve measurement unit where the curved state detection unit is provided by stronger force than force applied on the part where the curved state detection unit is not provided.

4. The curve sensor according to claim 1, wherein at least one radially piercing slit is formed in at least one of the circumferential walls of the first and second holding members, and
the part of the curve measurement unit where the curved state detection unit is provided is held by the parts of the first and second holding members where the slit is not formed.

5. The curve sensor according to claim 1, wherein the holding portion comprises holding members that are located apart from each other, and
the holding members are coupled to each other by at least one of the light supply unit and the curve measurement unit.

6. The curve sensor according to claim 1, wherein the light supply unit and the curve measurement unit comprise one optical fiber, and
the light transmission unit is a turnover produced by folding the optical fiber.

7. The curve sensor according to claim 1, wherein at least part of the curve measurement unit also serves as the light supply unit.

8. The curve sensor according to claim 7, wherein the curve measurement unit which at least partly also serves as the light supply unit comprises one optical fiber, the curve sensor further comprising an optical connector which guides light from a light source that emits light having a predetermined optical characteristic to the curve measurement unit and which guides light from the curve measurement unit to a light receiving unit, the optical connector being connected to a first end of the optical fiber, a reflecting portion which reflects light in the optical fiber being formed at a second end of the optical fiber as the light transmission unit.

9. The curve sensor according to claim 7, wherein at least parts of the light supply unit and the curve measurement unit comprise a flexible optical circuit board.

10. The curve sensor according to claim 1, wherein the holding portion is a flexible optical circuit board.

11. The curve sensor according to claim 10, wherein an extension optical fiber is connected to at least one end face of the flexible optical circuit board.

12. The curve sensor according to claim 10, wherein the curved state detection unit is formed on the flexible optical circuit board by printing.

13. The curve sensor according to claim 1, wherein a light receiving unit which receives a signal regarding the curved state from the curve measurement unit and a light source which supplies light to the light supply unit are housed in a same case provided outside the measurement target.

14. The curve sensor according to claim 13, wherein a member which connects the curve measurement unit to the light receiving unit which receives the signal regarding the curved state from the curve measurement unit, and a member which connects the light supply unit to the light source which supplies the light to the light supply unit are bundled.

15. The curve sensor according to claim 1, wherein at least one of a light receiving unit which receives a signal regarding the curved state from the curve measurement unit and a light source which supplies light to the light supply unit is connected by an attachable and detachable connector.

16. A curve sensor which measures curving of a curving measurement target, the curve sensor comprising:
  a light supply unit which guides light;
  a curve measurement unit which comprises a curved state detection unit and which is configured to measure a curved state of the measurement target by a change in an amount of light output through the curved state detection unit;
  a light transmission unit which transmits the light from the light supply unit to the curve measurement unit; and
  a holding portion which holds the light supply unit and the curve measurement unit at a predetermined position on the measurement target,
  wherein the holding portion comprises an elastic member which holds the light supply unit and the curve measurement unit at the predetermined position on the measurement target by elastic force, the elastic member comprising:
    a cylindrical first elastic member, and
    a cylindrical second elastic member, an outer circumferential surface of the second elastic member being engaged with an inner circumferential surface of the first elastic member, the measurement target being inserted into an inside of the second elastic member,
    wherein a cutout which permits the curve sensor to be attached to the measurement target from a side is formed in a circumferential wall of each of the first elastic member and the second elastic member.

17. The curve sensor according to claim 16, wherein the curved state detection unit is protected by the holding portion.

18. The curve sensor according to claim 16, wherein the holding portion is attachable to and detachable from the measurement target.

19. The curve sensor according to claim 18, wherein the light supply unit and the curve measurement unit are held at the predetermined positions of the holding portion without regard to whether the holding portion is attached to or detached from the measurement target.

20. The curve sensor according to claim 16, wherein the elastic member comprises a tapered portion on at least one end side for facilitating insertion of the measurement target into the one end side.

21. A curve sensor which measures curving of a medical device, the curve sensor comprising:
  a first optical fiber which guides light;
  a second optical fiber having a curved state sensor for measuring a curved state of the medical device by a change in an amount of light output through the curved state sensor;
  an optical device disposed between the first and second optical fibers for transmitting the light from the first optical fiber to the second optical fiber; and
  a holder for holding the first optical fiber and the second optical fiber at a predetermined position on an outer surface of the medical device, the holder comprising:
    a first cylindrical body, and
    a second cylindrical body, an outer circumferential surface of the second cylindrical body being engaged with an inner circumferential surface of the first cylindrical body, the medical device being inserted into an inside of the second cylindrical body,
    wherein the holder is configured so that at least one of the first optical fiber and the second optical fiber is held between the inner circumferential surface of the first cylindrical body and the outer circumferential surface of the second cylindrical body.

22. The curve sensor of claim 21, wherein the first cylindrical body comprises a cylindrical first elastic member which holds the first optical fiber and the second optical fiber relative to the second cylindrical body by elastic force.

23. The curve sensor of claim 21, wherein the second cylindrical body comprises a cylindrical second elastic member which holds the cylindrical second elastic member at the predetermined position on the outer surface of the medical device by elastic force.

24. The curve sensor of claim 21, wherein the holder comprises a cutout which permits the curve sensor to be attached to the medical device from a side, the cutout being formed in a circumferential wall of each of the first cylindrical body and the second cylindrical body.

25. The curve sensor of claim 21, wherein the optical device comprises a reflector.

26. The curve sensor of claim 21, wherein the optical device comprises a curved portion of optical fiber connecting the first cylindrical body and the second cylindrical body.

* * * * *